United States Patent [19]

Khan

[11] Patent Number: 5,654,408
[45] Date of Patent: Aug. 5, 1997

[54] MELANOMA-ASSOCIATED ANTIGENS IDENTIFIED BY MONOCLONAL ANTIBODIES

[75] Inventor: Amanullah Khan, Dallas, Tex.

[73] Assignee: Cytoclonal Pharmaceutics, Inc., Dallas, Tex.

[21] Appl. No.: 341,718

[22] Filed: Apr. 21, 1989

Related U.S. Application Data

[62] Division of Ser. No. 676,839, Nov. 30, 1984, Pat. No. 4,851,510.

[51] Int. Cl.$^6$ ............................ C07K 14/82; A61K 39/00
[52] U.S. Cl. .................. 530/395; 530/350; 530/388.85; 530/828; 424/185.1; 424/277.1
[58] Field of Search ........................... 530/350, 395, 530/828, 387, 388.85; 435/240.2; 424/185.1, 277.1

[56] References Cited

U.S. PATENT DOCUMENTS

| | | |
|---|---|---|
| 3,999,944 | 12/1976 | Grosser et al. . |
| 4,172,124 | 10/1979 | Koprowski et al. . |
| 4,196,265 | 4/1980 | Koprowski et al. . |
| 4,224,404 | 9/1980 | Viza et al. . |
| 4,331,647 | 5/1982 | Goldenberg . |
| 4,349,528 | 9/1982 | Koprowski et al. . |
| 4,361,544 | 11/1982 | Goldenberg . |
| 4,414,148 | 11/1983 | Jansen et al. . |
| 4,426,446 | 1/1984 | Thomson . |
| 4,427,653 | 1/1984 | Springer . |
| 4,590,071 | 5/1986 | Scannon et al. . |
| 4,693,966 | 9/1987 | Houghton et al. . |
| 4,851,510 | 7/1989 | Khan ............................ 530/387 |

OTHER PUBLICATIONS

Sofer, G. et al. 1983 Biotechniques Nov./Dec. 1983. pp. 198–203.

Aota, et al., "Monoclonal Antibody Against A Unique Antigen On Human Acute Promyelocytic Leukemia Cell Line (HL–60)," *Experimental Hemotology* 10:835–43 (Nov. 1982).

Aota, et al., "Monoclonal Antibody Against Myeloid Leukemia Cell Lines (KG–1)," *Cancer Research* 43:1093–96 (Mar. 1983).

Brooks, et al., "Human Lymphocyte Markers Defined by Antibodies Derived From Somatic Cell Hybrids," *Clinical Experimental Immunology* 39:477–85 (1980).

Brown, et al., "Indirect Iodine–125 Labeled Protein A Assay for Monoclonal Antibodies to Cell Surface Antigens," *Journal of Immunological Methods* 31:201–10 (1979).

Bumol, et al.., "Unique Glycoprotein–Proteoglycan Complex Defined by Monoclonal Antibody on Human Melanoma Cells," *Proceedings of The National Academy of Sciences U.S.A.* 79:1245–49 (Feb. 1982).

Burchiel, et al., "Heterogeneity of HLA–A,B,Ia–Like, and Melanoma–Associated Antigen Expression by Human Melanoma Cell Lines Analyzed With Monoclonal Antibodies and Flow Cytometry," *Cancer Research* 42:4110–15 (Oct. 1982).

Carrel, et al., "Common Human Melanoma–Associated Antigen(s) Detected by Monoclonal Antibodies," *Cancer Research* 40:2523–28 (Jul. 1980).

Chee, et al., "Mouse Monoclonal Antibody to a Melanoma–Carcinoma–Associated Antigen Synthesized by a Human Melanoma Cell Line Propagated in Serum–Free Medium," *Cancer Research* 42:3142–47 (Aug. 1982).

Herlyn, et al., "Monoclonal Antibodies in Cell–Mediated Cytotoxicity Against Human Melanoma and Colorectal Carcinoma," *European Journal of Immunology* 9:657–59 (1979).

Herlyn, et al., "Specific Immunoreactivity of Hybridoma–Secreted Monoclonal Anti–Melanoma Antibodies to Cultured Cells and Freshly Derived Human Cells," *Cancer Research* 40:3602–09 (Oct. 1980).

Imai, et al., "Monoclonal Antibodies to Human Melanoma–Associated Antigens," *Transplantation Proceedings* XII:380–83 (Sep. 1980).

Imai, et al., "Characterization of Monoclonal Antibodies to Human Melanoma–Associated Antigens," *Journal of The National Cancer Institute* 66:489–95 (Mar. 1981).

Johnson, et al., "Surface Antigens of Human Melanoma Cells Defined by Monoclonal Antibodies," *European Journal of Immunology* 11:825–31 (1981).

Khan, et al., "Mouse Monoclonal Antibody (WI–MN–1) Against Malignant Melanoma," *Cancer Research* 43:5868–72 (Dec. 1983).

Kohler, et al., "Continuous Cultures of Fused Cells Secreting Antibody of Predefined Specificity," *Nature* 256:495–97 (Aug. 1975).

Koprowski, et al., "Study of Antibodies Against Human Melanoma Produced by Somatic Cell Hybrids," *Proceedings of the National Academy of Sciences U.S.A.* 75:3405–09 (Jul. 1978).

Liao, et al., "Common Neuroectodermal Antigens On Human Melanoma, Neuroblastoma, Retinoblastoma, Glioblastoma and Fetal Brain Revealed by Hybridoma Antibodies Raised Against Melanoma Cells," *European Journal of Immunology* 11:450–54 (1981).

Seeger, et al., "Common Antigenic Determinants on Human Melanoma, Glioma, Neuroblastoma, and Sarcoma Cells Defined With Monoclonal Antibodies," *Cancer Research* 41:2714–17 (Jul. 1981).

(List continued on next page.)

*Primary Examiner*—Thomas M. Cunningham
*Attorney, Agent, or Firm*—Sidley & Austin

[57] ABSTRACT

A new cell line has been made which is capable of producing an antibody that reacts with melanoma associated tumors cells. Antigens capable of reacting with the new antibody have been isolated and characterized. Methods are disclosed for utilizing the antibody and antigen of the present invention and diagnostic procedures for determining the identity and extent of melanoma associated disease. The compositions of the present invention are disclosed to be useful in other immunological proceedures.

2 Claims, No Drawings

OTHER PUBLICATIONS

Steplewski, et al., "Reactivity of Monoclonal Anti–Melanoma Antibodies with Melanoma Cells Freshly Isolated from Primary and Metastatic Melanoma," *European Journal of Immunology* 9:94–96 (1979).

Ugolini, et al, "Initial Characterization of Monoclonal Antibodies Against Human Monocytes," *Proceedings National Academy of Sciences U.S.A.* 77:6764–68 (Nov. 1980).

Woodbury, et al, "Identification of A Cell Surface Protein, p–97, in Human Melanomas and Certain Other Neoplasms," *Proceedings of the National Academy of Sciences U.S.A.* 77:2183–87 (1980).

Bumol, T., et al., "Immunochemical and Biosynthetic Analysis of Monoclonal Antibody–Defined Melanoma–Associated Antigen," 1 *Hybridoma* 283–92 (1982).

Herlyn, M., et al., "Production and Characterization of Monoclonal Antibodies Against Human Malignant Melanoma," 1 *Cancer Investigation* 215–24 (1983).

Mattes, M., et al., "Monoclonal Antibodies to Three Widely Distributed Human Cell Surface Antigens," 2 *Hybridoma* 253–64 (1983).

Morgan, A., et al., "Monoclonal Antibodies to Human Melanoma–Associated Antigens: An Amplified Enzyme–Linked Immunosorbent Assay for the Detection of Antigen, Antibody, and Immune Complexes," 43 *Cancer Research* 3155–59 (1983).

Nepom, G., et al., "Induction of Immunity to a Human Tumor Marker by In Vivo Administration of Anti–Idiotypic Antibodies in Mice," 81 *Proc. Nat'l. Acad. Sci. U.S.A.* 2864–67 (1981).

Forstrom, J., et al., "Immunization to a Syngeneic Sarcoma by a Monoclonal Auto–Anti–Idiotypic Antibody," 303 *Nature* 627–29 (1983).

Suter, L., et al., "Heterogeneity of Primary and Metastatic Human Malignant Melanoma as Detected with Monoclonal Antibodies in Cryostat Sections of Biopsies," 16 *Cancer Immunol. Immunother.* 53–58 (1983).

Reisfield, Ralph A., "Monoclonal Antibodies to Human Malignant Melanoma," 298 *Nature* 325–26 (1982).

MELANOMA-ASSOCIATED ANTIGENS IDENTIFIED BY MONOCLONAL ANTIBODIES

This application is a division of Ser. No. 06/676,839, filed Nov. 30, 1984 now U.S. Pat. No. 4,851,510.

TECHNICAL FIELD

This invention relates to anti-tumor monoclonal antibodies and specifically to a monoclonal antibody which recognizes one or more antigenic sites on human malignant melanoma cells. This invention also relates to a manufactured hybridoma continuous cell line capable of producing said antibody and to the antigen(s) recognizable by said antibody which have been isolated and characterized. This invention further relates to the use of said antibody and/or said antigen for the production of certain other monoclonal or polyclonal antibodies. The antibody and antigen of this invention are also useful in diagnostic methods.

BACKGROUND OF THE INVENTION

Cancerous diseases are generally manifested by uncontrolled growth of cells that differ from the normal cells of the afflicted animal. Diagnosis and treatment of cancer have long been problematic. The disease is often far advanced before symptoms are evident, making treatment more difficult. In addition, the biopsy method of ascertaining whether cells are malignant requires surgery to remove a tissue sample and highly trained pathologists to observe the tissue under a microscope. Treatment of cancer has been hampered by both lack of adequate early detection methods and lack of selectivity of methods employed. Methods effective to eliminate cancer cells may also be harmful to normal cells. Since cancer cells of one type of disease such as leukemia may differ from cancer cells of other types of disease such as malignant melanoma, treatment could be better tailored to the disease if the technological capability to differentiate cancer cells from normal cells, or among types of cancer cells, existed.

The art has revealed that immunologic differences may exist between cells. The present invention concerns the discovery of an immunologic difference between normal cells and cancer cells that has never before been described and the making of a composition useful for manufacturing antibodies for detecting this difference.

A mammalian immune system generally operates to "respond" to matter that is not part of the normal cells of the organism. This matter is sometimes described as "non-self". One response made by the immune system may be to cause lymphocytes to produce antibodies that can specifically react with sites on the "non-self" matter (antigenic sites). Each unique lymphocyte produces unique antibodies. Each individual antibody molecule may be able to react only with a particular antigenic site. Normal cells may have some antigens that are also found on cancer cells. Therefore one antibody produced by a mouse lymphocyte, for example in response to injection of the mouse with a human cancer cell, could possibly react with both normal and cancerous human cells. Another mouse lymphocyte could simultaneously produce an antibody directed against an antigen on the injected tumor cell that is unique to that tumor cell. This antibody would not react against antigens on normal human cells. Collectively, the mouse's many lymphocytes would produce a variety of different antibodies in response to the many antigens of the injected cell. It is desirable to isolate only the lymphocyte(s) which produce anti-tumor antibody.

Once appropriate lymphocyte(s) have been isolated, procedures are known for making them into monoclonal antibody "factories". A "monoclonal" antibody is derived from man-made technology in which a single antibody-forming cell is fused with a myeloma cell to form a "hybridoma". A hybridoma has a theoretically infinite life span and produces only one antibody type, each antibody molecule produced being identically specific for a certain antigenic site. With appropriate selection procedures, an anti-tumor antibody-forming cell line may be manufactured. The art has revealed the production of anti-tumor monoclonal antibodies and anti-melanoma-associated antigens via hybridoma techniques.

The present invention concerns the manufacture of a unique hybridoma. The hybridoma of the present invention is a continuous cell line capable of producing a monoclonal antibody, also a subject of the present invention. The monoclonal antibody, which has been named "WI-MN-1", has not been previously described. It has been found to specifically recognize certain antigenic sites of tumor cells, primarily located on melanoma cells. The antigens, never before described, have been isolated and characterized and are also a subject of the present invention.

Prior to the present invention, there has been no report of monoclonal antibodies recognizing these antigens. The monoclonal antibody of the present invention recognizes antigens on cells of some types of tumor tissue but not others. This property makes the monoclonal antibody of the present invention useful for diagnosis of and differentiation of cancerous disease. The specificity of the antibody for tumor antigens and lack of reactivity with normal cells indicate utility for treatment of disease by either antibody injection to counteract tumor antigen or by coupling the antibody to tumor-destroying drug, tumor toxins, or radioactive substances, and allowing the antibody to direct the coupled material to the tumor. Binding a radioactive substance to the antibody is effective in allowing physicians to locate the cancerous cells in the body by using imaging techniques, such as, for example, the gamma camera. The antibody directs the radioactive substance only to certain tumor cell antigens where the radioactive substance emits radiation detectable by non-surgical isotope detection methods. The antibody's specificity also allows for utility in isolation of antigen.

The antigens of the present invention have not been previously described. These antigens can be used in diagnostic tests to monitor natural antibody levels. By elucidating which tumor cells have this antigen, a key to the mechanism of malignant disease may be found. Because antigens may not be located on the surface of a cell, where they would be amenable to reaction with antibody, during the entire stage of cell life, monitoring the characterized antigen of the present invention may indicate the stage of or progression of disease. The antigen of the present invention has been found to be present on mainly large-sized cells and thus can be a marker for cell size differentiation. Tumor cells are also known to slough antigens into body fluids, such as the blood, urine, cerebral spinal fluid, peritoneal fluid, pleural fluids or others. The identification and quantitation of an antigen known to be associated with melanoma cells is significant in that it is now possible to monitor the antigen by testing fluids from the body to indicate the size of tumors, as larger tumors would theoretically slough more antigens into body fluids. Also, if a tumor were surgically removed, subsequent monitoring of the body fluids for the presence of melanoma-associated antigens could indicate whether all the tumor was successfully removed. Whether a tumor was successfully eradicated by chemotherapy or radiation could also be monitored by assessing antigen levels. Recurrences of the tumor could be detected by running tests on fluids for the antigen. In such monitoring tests, immunologic (such as enzyme-linked immunosorbent and radioimmunoassay) as well as other protein identification methods would be appropriate to identify the melanoma-associated antigen. Demonstration of melanoma antigen on tissues can be used to distinguish melanoma from normal tissue or other tumors. The antigen can also be used to elicit a specific antibody response. Rather than injecting an animal with whole tumor cells, which would elicit production of numerous antibodies to tumor and non-tumor antigens, the specific antigen of the present invention can be used to elicit a specific immunological response to known melanoma-associated antigen. Antigens are useful in vaccines to induce the development of immunity. Anti-tumor antibody can be isolated and purified with techniques employing tumor antigen.

The continuous cell line manufactured, which is a subject of the present invention, produces monoclonal antibodies to specific tumor antigen of the present invention. The cell line which has been deposited produces one monoclonal antibody able to recognize the described antigen. Other cell lines may now be easily manufactured because of the present invention which will produce antibodies with the same specificity, and these cell lines are encompassed by the present invention.

SUMMARY OF THE INVENTION

The present invention encompasses novel continuous cell line(s) for the production of monoclonal antibodies specific to certain tumor antigens, novel antibodies that specifically recognize tumor-associated antigens, and tumor-associated antigens that are recognized by the monoclonal antibodies produced by said cell lines.

One aspect of the present invention relates to a continuous cell line which produces antibodies which do not combine with normal human cell surface antigens but do combine specifically with certain sites on tumor antigens. The antigen containing such sites is apparently on most if not all melanoma-type cells. As isolated from the G-361 melanoma cells, the antigens with which the antibody (produced by the continuous cell line) combines have a molecular weight of about 105,000 or about 38,000 as determined by sodium dodecyl sulfate gel electrophoresis. One continuous cell line was deposited with the American Type Culture Collection 12301 Parklawn Drive (Rockville, Md., 20852) on Nov. 30, 1984 (ATCC #HB8672 ). Upon disclosure of ATCC #HB8672, it will be evident to those skilled in the art how to make continuous cell lines which produce antibodies with the same specificity.

Another aspect of the present invention concerns a monoclonal antibody (WI-MN-1) produced by ATCC #8672. Still another aspect of the present invention concerns monoclonal antibodies with the same specificity as WI-MN-1 produced by cells manufactured by using the WI-MN-1 antibody. Still another aspect concerns polyclonal antibodies obtained via a process utilizing WI-MN-1.

This invention also concerns a substantially pure antigen which can bind to WI-MN-1 antibody. As isolated from G-361 melanoma cells, said antigen has a molecular weight of about 105,000 or about 38,000 as determined by sodium dodecyl sulfate gel electrophoresis.

The compositions of the present invention are also useful in certain methods. Thus one aspect of the present invention concerns a method for testing cells for the presence of surface antigens which are recognized by WI-MN-1, and are thus not normal cells. Another aspect of the present invention concerns isolating antigens from cells which bind to WI-MN-1. Still another aspect relates to utilizing the WI-MN-1 antibody to correlate antigen presence with cell tumor size. The antigens of the present invention may be used in a method to measure antibody titer. Additionally, antigens sloughed from tumors in patients can be collected from body fluids and their properties assessed for identification. The antigens of the present invention are useful in methods for characterizing these sloughed antigens by using the claimed antigens as comparative standards in protein characterizaion procedures. Antibodies of the present invention can also be used in methods of identifying sloughed tumor antigens.

DETAILED DESCRIPTION OF THE INVENTION

I. Manufacturing the Continuous Cell Line

In manufacturing a continuous cell line, a "line" being cells that may be cultured in vitro having an infinite life span, that is capable of producing monoclonal antibodies, lymphocytic cells of a non-immunosuppressed mammal are first sensitized, as will be more fully described. Sensitized lymphocytes are then collected from the animal and fused with a myeloma cell. The resulting cell has the characteristics of both the myeloma cell, which is able to grow as a continuous cell line, and the sensitized lymphocyte which produces antibodies, and is known in the art as a "hybridoma" because it is a hybrid between the two types of cells. Convenient animals to use for obtaining sensitized lymphocytes are those such as mice, rabbits, goats or other small mammals that can be easily handled in the laboratory. The age of the animal is to be selected in accordance with profiles relating age to peak immune response that may be found in the literature.

Sensitized lymphocytic splenocytes are lymphocytes found in the spleen which are capable of producing antibodies. They are made amenable to producing specific antibodies that will recognize certain antigens by exposure to a "non-self" antigen, an antigen not normally found on that animal's own, normal cells. "Exposure" can be accomplished in several ways. One convenient way is to inject antigen directly into the animal's bloodstream by intravenous (i.v.) injection. Other injection routes can also be used. The intraperitoneal (i.p.) injection route is often used for subsequent exposures after an initial i.v. dosage. To induce increased sensitization of lymphocytes, and thus increase production of specific antibodies, the subject animal is to be exposed to the antigen of interest over a period of time. The more pure the antigen, the higher the likelihood that more cells will produce antibodies that will recognize that antigen. Whole tumor cells can be injected to elicit antibody production against cell surface antigens. Alternatively, smaller sections of tumor cell membranes or single antigens can be injected. An antibody is said to "recognize" an antigen when it exhibits some degree of binding affinity for that specific antigen in excess of affinity exhibited for a non-specific antigen. A tumor cell's surface contains numerous antigenic sites, some that may be the same as normal cell antigens, some that may be common to all tumor cells, and some that may be specific to the particular type of tumor cell. If a whole cell is injected, in fact many antigens are injected and it is likely that many antibodies will be produced exhibiting different specificity. In contrast, if one antigen is used to elicit antibody response, the likelihood is higher that more cells will produce antibodies specific to just that antigen. Selection of the antigen for injection should therefore take into account the specificity of antibody response desired. In the instant case, human malignant melanoma cell line G-361 (American Type Culture Collection, Rockville, Md.) was used as an antigen to induce antibody production to melanoma-associated antigen. Other melanoma cells can also be used as an antigen, and as previously noted isolated antigens from tumor cell membranes can be used if a more specific antibody response is desired. Example I shows the dosage of and time frame for injections found successful for inducing anti-melanoma antibody formation in the instant case. However, other dosages and time frames may be equally effective. Dosage is generally chosen by % bodyweight of the animal to be used. About $1 \times 10^7$ cells per 20 grams of animal is one effective dosage, but there are others. Depending on the animal used, antibody forming cells may be harvested from preferably about 3 days to about 14 days after the final injection. The peak day to harvest cells may be determined by testing a sample of the animal's serum for antibody titer (concentration) by reacting the serum with the antigen used for injection. Detection of antibody-antigen reaction can be done by any known method. The BALB/c mouse usually exhibits adequate response four days after the final injection. Splenocytes (lymphocytic) are most convenient to harvest; however, other antibody-forming cells may be used. "Harvesting" is accomplished by removing the sensitized animal's spleen and suspending the spleen tissue appropriately for the fusion procedure. One effective method is set out in Example I.

After obtaining antibody-forming cells from sensitized animals, a hybridoma is manufactured by fusing the antibody-forming cell with a myeloma cell, which imparts the infinite lifespan characteristic to the cell. There are several myeloma cells that are suitable for the hybridoma technique. The present invention requires fusion of the particular antibody forming cell with any cell capable of imparting the infinite lifespan characteristic to the resulting fused cell. Fusion can be done by any known technique.

The hybridoma specific for production of antibodies against melanoma antigens must be selected from all the hybridomas created. Several methods can be used such as immunofluorescence, radiolabeling and others. One method is to test for reactivity against the antigen of interest by an enzyme-linked immunosorbent assay, the method used in Example I.

II. Production of Antibodies

A single cell hybridoma that releases an antibody product which tests positive for reaction against the antigen of interest can be propagated in vitro cell culture or in vivo in animals. In the instant case, clones were propagated in mice by priming the mice with 2,6,10,14-tetramethylpentadecane, a substance known to promote plasmacytogenesis-increased formation of antibody-producing cells. Hoogenraad, *Journal of Immunological Methods* 61:317–320 (1983). The antibody-containing ascitic fluid can be used as a source of antibodies to test for specificity against (binding with) antigens of various tissues. Alternately, hybridoma cells can be grown in vitro. These cells exude antibodies which can be collected from the media. Since one clone is propagated into many, a great quantity of antibodies can be obtained that are identical. The monoclonal antibody thus obtained has been named "WI-MN-1."

This invention is intended to encompass any monoclonal antibody specific for the antigen herein discovered. For example, chemical modifications could be made to the antibody molecule of the present invention that do not alter its ability to recognize melanoma-associated antigen. The monoclonal antibody's amino acid sequence could be determined by techniques known in the art and an identical or almost identical molecule could possibly be synthesized that serves the same function as the monoclonal antibody exuded by the hybridoma cell of the present invention. Production of specific antibodies is also possible by injecting an animal with the specific antigen herein discovered. An animal capable of immune response will produce antibodies when injected with non-self antigen. Fluids or tissues from the animal will contain antibodies. For example, the blood may be taken from an immunized animal and serum antibodies isolated by immunoprecipitation with specific antigen. The preferred method of obtaining the antibody of the present invention is from the hybridoma cell.

III. Isolation of Antigens

Antigens that will specifically be recognized by the antibodies of the present invention can be isolated from cells exhibiting reactivity with the antibody. Reactivity can be tested by any suitable method including, but not limited to immunofluorescence, radiolabeling of a part of the antibody (so that any antigen-antibody complex formed will be radioactive and discernable by, but not limited to, such methods as scintillation counting, radioimmunoassay, or radioimmunoelectrophoresis), immunoprecipitation, immunoperoxidase staining, and/or enzyme-linked immunoabsorbant assay. Proper conditions for binding to Occur are pH of about 7.2 and physiological osmolarity. To achieve proper conditions, cells from which the antigen specific to the WI-MN-1 antibody is to be isolated are suspended in phosphate buffered saline [hereinafter PBS] (8.0 g NaCl, 0.2 g KCl, 1.5 g $Na_2HPO_4$, 0.2 g $KH_2PO_4$ in one liter deionized water pH 7.2). Table III-1 of Example III-1 shows the reactivity of monoclonal antibody "WI-MN-1," produced by the cell line of the present invention, against tumor cell lines. Five positive reactions were obtained. Table III-2 of Example III shows reactivity of WI-MN-1 monoclonal antibody against surgically removed metastatic malignant melanoma specimens. Positive reactions were obtained between the antibody and tissues obtained from fifteen of sixteen tested patients. Biopsies confirmed the presence of melanoma. Neoplastic tissue tested from other surgical specimens did not react with WI-MN-1 (Table III-3). Tables III-4 and III-5 show that the antigen was apparently not present on the cells of normal tissue. Therefore, normal tissues should not be used to isolate the antigen of the present invention. However, normal or cancerous tissues and body fluids can be tested for presence or absence of the antigen and thus this method is also applicable to diagnostic procedures.

Example III-I shows a procedure for isolating the antigen specifically recognized by the monoclonal antibody of the present invention, using as a source one of the positively-testing cells, malignant melanoma cell line G-361 (ATCC). The antigen, or at least an antigen with a similar combining site could, however, be isolated from any positively-testing cell by the same or other techniques such as protein purification methods. After obtaining the antigen-containing samples testing positive for reactivity against WI-MN-1 as determined by enzyme linked immunoabsorbent assay as per Example III-2, or by some other test for antibody-antigen reactions as previously noted, the antigen can be characterized. The molecular weight of the antigens that can be bound to WI-MN-1 antibody can be determined by any known method for molecular weight determination. A convenient method, as shown in Example III-3, is sodium-dodecyl-sulfate polyacrylamide gel electrophoresis (SDS-PAGE). Different methods of molecular weight determination may lead to slightly different results.

The isolated antigen is useful as a diagnostic standard against which patient body fluids or tissues may be compared. Presence of an antigen with like properties in a patient indicates that a tumor may be present. Characterization techniques for macromolecules, employing the antigen of the present invention as a standard, including but not limited to SDS-PAGE are part of the claimed method of using the antigen of the presant invention.

To further elucidate the role of the isolated antigen(s) in tumor cells, cell sorter analysis can be performed. This technique shows what size of tumor cells exhibit the surface antigen. In Example III-4, malignant melanoma cells from a pleural effusion were analyzed. Cell sorter instruments generally measure fluorescence; therefore, the antibody-antigen complex (the antigen being a whole cell in this instance) must be made fluorescent. There are two methods for fluorescent marking. One method, known as the "direct" method is to conjugate the specific antibody (here WI-MN-1) to fluorescein. If WI-MN-1 binds to an antigen on the surface of a cell, that cell will be measurably fluorescent. "Indirect" immunofluoresence can also be used. In this method, WI-MN-1 would not be conjugated to fluorescein. WI-MN-1 would bind to any antigen it is capable of recognizing on a cell surface. Then a fluorescein-conjugated antibody capable of recognizing the WN-MN-1 antibody as an antigen would be added. There would be measurable fluorescence if such a cell WN-MN-1 fluorescent antibody complex were formed. Both methods are effective. Cells can be observed under a fluorescence microscope or by instrumentation. In addition, other methods for marking the antigen so that its presence or absence can be assessed may be used, followed by visual observation of cell size. Because the antigen of the present invention was found to be mainly at large cell surface sites, an additional utility is evident for the antigen. It may be useful in tracking the cell size composition of disease tumors.

An antigenic composition is a composition which is capable of causing an immunological response to occur. The antigen that was isolated by reaction with WI-MN-1 from G-361 malignant melanoma cell lines is isolatable from any cell containing that antigen by comparable methodology. An antigen having the same recognition site is also isolatable with comparable methodology. To date, melanoma cells, epidermoid carcinoma cells, and amnion cells have tested positive for an antigen or antigens having the same recognition site. Acute myelomonocytic leukemia has tested weakly positive. These positively testing cells may contain the antigen, or at least an antigen with the same recognition site.

EXAMPLES

[Note: "Phosphate buffered saline" or PBS as referred to in all examples is: (8.0 g NaCl; 0.2 g KCl; 1.15 g $Na_2 HPO_4$, 0.2 g $KH_2 PO_4$ in 1 liter deionized water, pH 7.2)]

EXAMPLE I

Manufacturing a Hybridoma which Produces Anti-Melanoma Antibodies

Eight-week old BALB/c mice (obtained from Timeco, Houston, Tex.), about 20 grams each, were immunized with a preparation of G-361 human malignant melanoma cell line (obtained from the American Type Culture Collection (ATCC), Rockville, Md.). The immunization suspension was prepared by suspending the G-361 cells in Roswell Park Memorial Institute Medium (RPMI) (available from Grand Island Biological Co., Grand Island, N.Y. 14072 (GIBCO) to a concentration of $1 \times 10^7$ cells per 0.2 cc. A 26 gauge needle was used to administer a dose of $1 \times 10^7$ cells (i.v.) in a volume of 0.2 cc. Eight subsequent injections of $1 \times 10^7$ cells each were given to the mice (i.p.) every 10 days over nine weeks. Four days after the final injection, the mice were killed by stunning followed by rapid severing of the spine/head connection and their spleens rapidly removed after surface sterilization of the animals' ventral side with a disinfectant (Amphol) followed by ethanol. A preparation of splenocytes made by transferring the spleen to a sterilized screen (37 µm nylon mesh) and gently teasing it with a sterile syringe into a single cell suspension. The suspension was then washed twice with RPMI. The concentration of cells per milliliter was determined by counting with a hemocytometer. P-3NS-1/1Ag 4-1 myeloma, ATCC #T1B18 (American Type Culture Collection, Rockville, Md.) cells were hybridized with the splenocytes to form hybridomas by washing the myeloma cells twice with RPMI 1640 (RPMI) medium, then suspending in RPMI to a concentration of about $1 \times 10^7$ cells/ml. The suspension of splenocytes ($1 \times 10^7$ to $1.5 \times 10^7$ cells/ml) was then mixed with the suspension of myeloma cells (equal volumes). The mixture was then centrifuged at 409×g for 10 minutes. The supernatant was removed, and the tube placed in a 37° C. bath. One ml of 50% w/v polyethylene glycol, cell culture reagent grade pretested for cytotoxicity (available from ATCC) in RPMI was added to the pellet. The pellet was then gently stirred with a 1 ml pipette for two minutes. One more ml RPMI (37° C.) was added to the pellet followed by stirring for 1 minute. An additional ml RPMI (37° C.) was added followed by stirring for one minute. Seven mls RPMI (37° C.) were then added followed by two to three minutes stirring, centrifugation at 400×g (10 minutes), and removal of the supernatant. Ten mls of RPMI with 15% horse serum (serum screened for hybridoma growth by and purchased from Irvine Co., Santa Ana, Calif. 92705) was added slowly with gentle stirring and mixing with a 10 ml pipette. The volume was adjusted to 40 mls with RPMI with 15% horse serum. 0.1 ml of this solution was added to each well of four microtiter plates (Costar 96 well plates) for a total of three hundred and eighty-four wells. The plates were incubated at 37° C. in a humidified incubator, 5% $CO_2$ until the following day (Day One). Day One: Fused myeloma-lymphocytes were selected for by adding 0.1 ml of 1× hypoxanthine-thymidine-aminopterin (HAT) solution in which unfused myeloma cells cannot survive. 1× HAT solution was prepared by diluting 50× HAT solution (50 mls of a solution containing 0.1361 g hypoxanthine and 0.0388 g thymidine in 100 ml deionized water added to 5 mls of a solution containing 17.6 mg aminopterin in 0.1M NaOH required to dissolve it brought to 100 mls with deionized water, brought to 100 mls with 45 mls of deionized water) with RPMI 1640 medium containing 15% Horse Serum.

Day 3: 100 microliters of medium was removed from each well then 100 microliters of 1× HAT was added.

Day 5: 100 microliters of medium was removed from each well then 100 microliters of 1× HAT was added.

Day 7: Unfused spleen cells died.

Day 10: Hybridoma medium was added ( 1× Hypoxanthine-Thymidine solution plus 15% Horse Serum). [hereinafter "HT medium"]

Day 14: Hybridoma cells were seen. When 30–60% of a well contained growing hybridomas, the antibody testing procedure was begun. At this point in the procedure, each well contained a mixture of different hybridoma cells, each possibly producing different antibodies. The supernatant containing the exudate from the mixture of hybridoma cells was screened to identify wells containing a hybridoma specific for production of anti-melanoma antibodies. The selection procedure involved testing the hybridoma's antibody products for reaction against G-361 melanoma cells by the enzyme-linked immunoabsorbent assay. This assay was done by adding $1\times10^5$ G-361 cells to wells of polyvinyl chloride microtiter plates that had been pretreated with poly L-lysine for 2 hours at 25° C. then washed and allowing the cells to be fixed to the plate surface by centrifuging the plates for 5 minutes at 1000 R.P.M. (Model GLC-2 centrifuge from Sorvall, Newtown, Conn.; Centrifuge plate carrier from Dynatek Laboratories, Alexandria, Va.) then adding 0.2% glutaraldehyde in phosphate buffered saline and incubating 15 minutes at room temperature. The glutaraldehyde was removed by washing. A 1% solution of bovine serum albumin (BSA) (Sigma, St. Louis Mo.) in phosphate buffered saline was then added to each well along with 100 microliters of 100 mM glycine for 30 minutes at 25° C. The wells were then washed twice with phosphate buffered saline to remove non-bound BSA. Fifty microliters of hybridoma supernatant (fluid obtained from wells in which hybridomas were grown) were added to each G-361 well. Negative control wells were set up in which no hybridoma supernatant was added but gamma globulin antibody known not to react with melanoma was added. Positive control wells were set up in which serum from mice immunized against G-361 cells was added in lieu of hybridoma supernatant. The serum was prepared by centrifuging at 400×g for 10 minutes. The G-361 plate was then incubated at 37° C. in a humidified atmosphere for 2 hours (in a standard cell culture incubator). After incubation, an enzyme-linked immunoabsorbent (ELISA) assay was done by then emptying the plate and tapping dry, washing once by filling each well with 0.3 ml of wash solution (a 1:10 dilution of the wash solution concentrate supplied with the kit (Hybri-Clonal™ Mouse G ELISA screening kit for monoclonal antibodies) obtained from Kirkegaard & Perry Laboratories, Inc.; Gaithersburg, Md. which contains Tween 20 as supplied) then emptying and tapping dry. Horseradish peroxidase-labeled antibody to mouse gamma globulin was then added to each well (supplied with kit described above). The washing step was repeated five additional times. After the final tap dry step, 0.02 milliliters peroxidase substrate solution (2,2'-azino-di[3-ethyl-benzthiazoline sulfonate (6)]) (prepared by mixing 2.5 mls solution A and 2.5 mls solution B from the kit) was added. The reaction was assessed by visually observing (positive wells turn blue-green) or by using an instrument to measure absorbance at 414 nm. Absorbence measurements were made on a Titertek Multiscan (Flow Laboratories, McLean Va.) using a 414-nm filter. Test wells exhibiting a two fold or greater increase in absorbence as compared to a negative control were considered "positive". Hybridomas from wells which had produced the supernatant testing "positive" were then cloned by the limiting dilution technique. The limiting dilution technique consisted of putting about 0.1 ml of each ml positively-testing hybridoma suspension in 10 mls HT medium and plating 0.1 ml of this mixture into each well of new plates, the objective being to obtain only one cell per well. The wells were each given 0.5 ml additional HT medium. Once this was accomplished, each well's supernatant was retested by the ELISA method described above to identify the specific hybridoma that produced anti-G-361 melanoma antibodies, after the plated initial hybridoma cell propagated to about 30–60% of the well.

EXAMPLE II

Production of Monoclonal Antibodies

Hybridoma clones selected for production of anti-melanoma antibodies were propagated in vivo in mice. Eight to ten week old mice were primed with 2,6,10,14-tetramethyl-pentadecane (Sigma Chemical Co., St. Louis, Mo.), sterilized by passage through a 0.22 micron sterile filter, by i.p. injection (0.5 cc as purchased). The clone was then introduced to the mouse by i.p. injection after two weeks. Ascites fluid, presumably containing antibodies produced by the hybridoma clones, was withdrawn from the mouse peritoneal cavity after 10–14 days. The fluid was used as the source of antibodies. Since the ascites fluid also contained hybridoma cells, the fluid was centrifuged at 400×g (10 min) to obtain cell-free antibody-containing fluid.

EXAMPLE III-1

Demonstration of Specific Antigens on Cells

The presence or absence of the antigen capable of binding to WI-MN-1 was demonstrated by indirect immunofluorescence according to the method of Aota et. al. 43 *Cancer Research* 1093–1096 (1983) and Brooks et. al. 39 *Clin. Exp. Immunol.* 477–485 (1980). Fluorescein-conjugated goat anti-mouse gamma globulin was purchased from the Meloy Co. (6715 Electronic Dr. Springfield, Va. 22151). The total protein concentration of the Meloy commercial preparation and the fluorescein to protein (F/P) ratio was determined by reference to the assay data contained on the package insert. A series of dilutions was made to determine a working dilution for the particular vial used. A 1:10 dilution of the commerically obtained preparation in phosphate buffered saline, pH 7.2 was used [the original having an F/P ratio of about 2.5 to 2.9.]. Fifty microliters of a suspension of cells in phosphate buffered saline to be tested for antigen ($5\times10^5$ cells total) was fixed to a microscope slide. Fifty μl of a 1:100 dilution of ascites fluid supernatant was added to the slide. The reaction was allowed to proceed for 30 minutes at 4° C. The slide was then washed twice with phosphate buffered saline. Fifty μl of the fluorescein conjugated serum (the 1:10 dilution prepared above) was added to the slide. Reaction was allowed to occur for 30 minutes at 4° C. The slide was then washed twice with phosphate buffered saline and observed under the fluorescence microscope [absorption 495 nm and emission 525 nm]. Positive fluorescence indicated that the cells tested had an antigenic site capable of binding to the WI-MN-1 antibody obtained from the hybridoma cells made in the present invention.

Indirect ABC Immunoperoxidase staining was also done to check for reactivity of WN-MN-1 against fresh tissue sections according to the method of Hsu, et al 75 *Am. Society of Clinical Pathology* 734–738 (1981). The fresh tissue sections were prepared by plunging them immediately into liquid nitrogen and cutting to a 6 micron thickness with a cryostat at −20° C. The tissue was fixed to a slide by using cold acetone. The slide was then subjected to a washing procedure after being placed in a Coplin jar. The slide was first washed with a 1:100 dilution of a fresh solution (198 mls. methanol plus 2 mls. 30% $H_2O_2$) for 10 minutes. This solution was decanted and the slide washed with phosphate buffered saline (PBS) for 10 minutes. The slide was then removed from the jar and treated with 100–200 µl (enough to cover tissue) of a 1:10 dilution in PBS of normal horse serum with 0.1% bovine serum albumin for 15 minutes. The slide was then covered with a 1:100 dilution in PBS of mouse ascites fluid (in which WI-MN-1 monoclonal antibody was propagated) for 30 minutes. The slide was then dipped in a fresh PBS bath several times, then allowed to sit in a PBS bath for 15 minutes. A 1:500 dilution of biotinilated anti-mouse antibody (obtained from Vectastain Kit, Vector Laboratories, Inc., Burlingame, Calif. 94010) (diluted in PBS with 0.1% bovine serum albumin) was then put on the slide to cover the tissue for 30 minutes. The slide was then dipped in a fresh PBS bath, followed by allowing the slide to remain in a PBS bath for 10 minutes. Avidin-Biotin-Complex (ABC) solution was prepared by adding 50 µl of 10% BSA to 5 ml of PBS (0.1% BSA), one drop of reagent A which is Avidin DH and one drop of reagent B which is Biotinylated Peroxidase from the Vectastain Kit, and allowing the mixture to stand 5 minutes. The slide was incubated in ABC for 30 minutes, then washed with PBS for 10 minutes. A stock solution of Diaminobenzedene (DAB) (6 mg/ml) was prepared and stored at −20° C. A 1:10 dilution of stock DAB in PBS was made at assay time, incubating at room temperature for 30 minutes (Solution A). Ten microliters of 30% $H_2O_2$ was added to 590 microliters of PBS (Solution B). One hundred µl of solution A was added to 5 mls Solution B and filtered through a 0.45 µm millipore filter to form Solution C. All solutions containing DAB were shielded from light. The slide was incubated with Solution C for 3 to 5 minutes, followed by washing for 10 minutes in a fresh PBS bath. The slide was then dipped 1 time for 1 minute in hematoxylin, followed by 10–40 dips in 4% acetic acid, followed by 10 dips in distilled $H_2O$, 20 dips in saturated $LiCO_3$, 1 minute in distilled water, 2 minutes in 70% ethanol, 2 minutes in absolute ethanol, 2 minutes in fresh absolute ethanol, 2 minutes in xylene, 2 minutes in fresh xylene, and finally Permount (obtained from Fisher Scientific, Fair Lawn N.J. 07410) was placed on the slide and a coverslip applied. The presence of antigen was detected by observing the treated slide under the microscope at 100× power and looking for a brown chromogen (DAB) precipitated at the site of antigen.

TABLE III-1

Cell lines tested for binding
with WI-MN-1 by indirect immunofluorescence

| Cell line | Cell type | Results[a] |
|---|---|---|
| G-361 | Malignant melanoma | 3+ |
| HT-144 | Malignant melanoma | 3+ |
| MeWo | Malignant melanoma | 3+ |
| Hep-2 | Epidermoid carcinoma | 3+ |
| WISH | Amnion | 2+ |
| Rc2a | Acute myelomonocytic leukemia | 1+ |
| A-549 | Lung carcinoma | — |
| HeLa | Cervical carcinoma | — |
| HT-29 | Colon carcinoma | — |
| BT-20 | Breast carcinoma | — |
| 734-B | Breast carcinoma | — |
| SW-1088 | Astrocytoma | — |
| K-562 | Chronic myelogenous leukemia | — |
| HL-60 | Acute promyelocytic leukemia | — |
| Molt-4 | Acute lymphocytic leukemia | — |
| Nalm-16 | Acute lymphocytic leukemia | — |
| KG-1 | Acute granulocytic leukemia | — |
| Daudi | Burkitt's lymphoma | — |
| Raji | Burkitt's lymphoma | — |
| Namalwa | Burkitt's lymphoma | — |

TABLE III-1-continued

Cell lines tested for binding
with WI-MN-1 by indirect immunofluorescence

| Cell line | Cell type | Results[a] |
|---|---|---|
| U-266 | Multiple myeloma | — |
| U-937 | Monocytic | — |
| L-929 | Mouse fibroblast | — |
| B-16 | Mouse melanoma | — |

[a]Intensity score fluorescence: —, no fluorescence above background; 1+, faint fluorescence; 2+, weakly bright fluorescence; 3+, moderately bright fluorescence; 4+, strongly bright fluorescence.

All cell lines are available from the American Type Culture Collection (Rockville, Md.).

TABLE III-2

Surgically removed
metastatic malignant melanoma specimens
tested with WI-MN-1 by indirect immunofluorescence

| Donor | Tissue | Result[a] |
|---|---|---|
| W. D. | Axillary lymph node | 1+ |
| W. D. | Nodule from shoulder | 1+ to 3+ |
| W. S. | Perianal tissue | 1+ to 3+ |
| R. W. | Bone marrow | 1+ (weak) |
| T. B. | Leg and ankle tissue | — |
| J. S. | Back tumor | 1+ to 3+ |
| J. S. | Arm tumor | 1+ to 3+ |
| C. C. | Infrascapular area | 2+ to 3+ |
| H. T. | Anterior chest node | 1+ |
| R. B. | Chest lesion | 1+ to 2+ |
| B. C. | Right inguinal lymph node | 1+ |
| W. L. | Presternal node | 1+ to 2+ |
| T. R. | Subclavicular lymph node | 1+ to 3+ |
| T. R. | Pleural fluid | 1+ to 2+ |
| L. D. | Chest wall nodule | 1+ to 2+ |
| K. H. | s.c. suprapubic nodule | 1+ to 3+ |

[a]Intensity score fluorescence: —, no fluorescence above background; 1+, faint fluorescence; 2+, weakly bright fluorescence; 3+, moderately bright fluorescence; 4+, strongly bright fluorescence.

TABLE III-3

Surgically removed
neoplastic tissue specimens tested
with WI-MN-1 by indirect immunofluorescence

| Diagnosis | Site of lesion | Results |
|---|---|---|
| Multiple myeloma | Bone marrow | —[a] |
| Ovarian carcinoma | Ascitic fluid | — |
| Ovarian carcinoma | Abdominal wall | — |
| Ovarian carcinoma | Omentum | — |
| Burkitt's lymphoma | Chest wall lesion | — |
| Breast carcinoma | Supraclavicular lymph node | — |
| Breast carcinoma | Pleural fluid | — |
| Ependymoma | Posterior fossa tumor | — |
| Acute granulocytic leukemia | Bone marrow | — |
| Renal cell carcinoma | Kidney | — |
| Medullary cancer of thyroid | Thyroid | — |
| Colon carcinoma | Omentum | — |

[a]—, negative.

TABLE III-4

Normal tissue tested for binding
with WI-MN-1 by indirect immunofluorescence

| Tissue | No. of tissues tested | Results |
| --- | --- | --- |
| Spleen | 3 | —[a] |
| Lymph node | 1 | — |
| Thymus | 1 | — |
| Lymphocytes | 3 | — |
| Monocytes | 1 | — |
| RBCs | 4 | — |
| Bone marrow | 2 | — |

[a]—, negative.

TABLE III-5

Autopsy tissues tested for binding
with WI-MN-1 by indirect immunofluorescence

| Tissue | Results |
| --- | --- |
| Breast | 1—[a] |
| Lung | — |
| Spleen | — |
| Stomach | — |
| Heart | — |
| Brain | — |
| Kidney | — |
| Liver | — |
| Testis | — |
| Skin[b] | — |

[a]—, negative.
[b]Tested by immunoperoxidase staining on frozen section.

EXAMPLE III-2

Isolation of Antigen

Antigen was isolated from human malignant melanoma cell line American Type Culture Collection #G-361 as follows: Cells were grown in Roswell Park Memorial Institute Medium 1640 (Grand Island Biological Co., Grand Island, N.Y.) [hereinafter RPMI-1640] with 10% fetal bovine serum (heat inactivated). The cells were washed during the log phase of growth with RPMI-1640 without serum. Cells were then detached with Trypsin in Dulbecco's 0.01% EDTA/phosphate buffered saline (KCl 0.2 g/l; $KH_2PO_4$ 0.2 g/l; $Na_2HPO_4.2H_2O$ 1.15 g/l or $Na_2HPO_4$ 0.905 g/l; NaCl 8.0 g/l; Trypsin 1:250 (obtained from DIFCO Finley, Ohio 45840) 2.5 g/l; EDTA 0.1 g/l) (approximately 10–15 ml/75 $cm^2$ flask). A pellet of cells was obtained by centrifuging at 400×g for 30 minutes. The pellet was washed with RPMI-1640 without serum. The pellet was extracted by adding extraction buffer (containing 0.5% NP-40 detergent (available from Sigma Chemical Co., St. Louis, Mo.)) in 10 mM Tris buffered saline buffer (1.27 g Trizma-HCl (Sigma); 0.236 g Trizma-Base (Sigma); 8.766 g NaCl; brought to 1 liter in deionized water and to pH 7.5); 1 mM phenylmethyl-sulphonyl fluoride in Tris buffered saline), vortexing, and allowing to sit for 15 min. on ice. The extractant was then transfered to microcentrifuge tubes and centrifuged for 20 min. at high speed (using a Brinkmann centrifuge 3200). The supernatant containing antigen was then collected and subjected to further purification steps. The antigen extract was dialyzed using 12,000–14,000 M.W. cut-off dialyzing membrane for 24 hrs against column buffer. [Column buffer is prepared as follows: Dissolve 0.1 g of $CaCl_2$ and 0.1 g of $MgCl_2$—$6H_2O$ in 100 ml of deionized water (solution A). Dissolve 0.2 g of KCl, 0.2 g $KH_2PO_4$, 1.15 g of $Na_2HPO_4$, and 8.0 g NaCl in 800 ml deionized water (solution B). Vigorously stir the solution B and slowly add solution A into it. Adjust the pH to 7.2–7.4 with 1N HCl. Bring up to 1 liter. Sterilize through 0.22 micron membrane]. The dialyzed antigen was applied to a Lentil-Lectin (E.Y. Laboratories, San Mateo, Calif.) column to isolate the detergent-solubilized membrane proteins from the detergent. The column was washed with Column Buffer until no more protein eluted from the column, as determined by a protein assay using the Bio-Rad reagents and method (Bio-Rad Co., 2200 Wright Ave, Richmond, Calif. 94804). Bound antigens were eluted with eluting buffer (0.1M α-methyl-D-mannoside in 1 liter of deionized water). Further purification of eluted antigen was carried out by affinity column chromatography.

The Affinity Chromatography procedure used was as follows:

Preparation & Coupling of antibody cyanogen bromide-activated sepharose 4B [hereinafter: CNBr activated sepharose 4B]: 1. The CNBr activated sepharose 4B was weighed (1 gm freeze-dried material gives about 3.5 ml final gel volume; 5–10 mg protein/ml swollen gel). 2. Freeze-dried powder was swollen for 15 min in 1 mM HCl and washed on a sintered glass filter (porosity G3) with 200 ml of 1 mM HCl per gram dry gel, in several aliquots. 3. The gel was then washed with coupling buffer (0.1M Na $HCO_3$+0.5M NaCl, pH 8.3) at an amount 5 ml/gram dry gel and immediately transferred to 7 mls of a WI-MN-1 antibody solution of 1:2 concentration in coupling buffer 4. After adding the gel to the antibody solution, it was mixed in an end-over-end mixer for 2 hrs at room temperature. 5. The remaining active groups were blocked by adding blocking buffer (0.2M glycine, pH 8.0) for 2 hrs., room temperature. 6. Excess adsorbed protein was washed from the column by using coupling buffer followed by acetate (0.1M $CH_3COONa$, 0.5M NaCl, pH 4.0.) buffer. This cycle was repeated 3 times. 7. The antibody-coupled column was pre-eluted with a. 40–50 ml of 100 mM diethylamine, pH 11.5
b. 40–50 ml of 1M Tris HCl, pH 8.2
c. 40–50 ml of column buffer (0.05 M Tris-HCl+0.5 NaCl, 1 mM EDTA, pH 8.2)

8. The Column was then ready for application of antigen from the Lentil-Lectin column.

Application of antigen: Eluted antigen from Lentil-Lectin column was dialyzed using 12,000–14,000 M.W. cut-off membrane for 24 hrs against the column buffer (0.05 Tris HCl+0.5M NaCl, 1 mM EDTA, pH 8.2). After dialysis the antigen was sterilized by passing it through a 0.22 micron membrane. The sample was then applied to the already coupled affinity column at a flow rate of approximately 0.2 ml/min. The column was then washed with 100–150 ml of column buffer, followed by 100–150 ml of borate buffer (1 mM Tris HCl, 10 mM boric acid, 25 mM sodium borate and 0.2% sodium dodecyl sulfate (SDS), pH 8.5). The antigen was eluted with 40–50 ml of 100 mM diethylamine, pH 11.5 at a rate of 0.25 ml/min. Two ml fractions were collected in test tubes containing 0.5 ml of neutralizing buffer (2M Tris-HCl, pH 7.2). Fractions were dialyzed using 12,000–16,000 M.W. cut-off natural cellulose dialysis tubing (Spectrum Medical Industries, Inc. Los Angeles, Calif. 90054) against phosphate buffer saline (PBS) (8.0 g NaCl, 0.2 g KCl, 1.15 g $Na_2HPO_4$, 0.2 g $KH_2PO_4$, pH 7.2). Dialyzed fractions were concentrated using 10,000 M.W. cut-off membrane (Type YMIO, AMICON Corp., Lexington, Mass. 02173) Fractions were tested for antigen using WI-MN-1 monoclonal antibody, by enzyme linked immunoabsorbant assay (ELISA) according to the following procedure:

Preparation of ELISA plate—50 microliters of affinity purified antigen was added to the 1st well of the 2nd row of an ELISA polyvinyl chloride (PVC) plate. The 1st row was left as a blank. Ten-fold serial dilution of antigen was made all the way down the 2nd row, using 0.1M sodium-carbonate, pH 9.6. That is, each successive well was a 10-fold dilution of the previous Well. Antigen was added to the 3rd and 4th row of the plate for controls, each successive well also diluted 10-fold, In the subsequently-described procedure, the WI-MN-1 antibody was not added to the third row, and non-specific antibody was added to the fourth row. Fifty microliters of 1M sodium-carbonate was added to all the wells. Fifty microliters of carbodiamide (1 mg/ml) was then added to each well. The plate was incubated at 4° C. overnight or 2 hours at room temperature. It was then washed 3 times with phosphate buffered saline (PBS) (8.0 g NaCl, 0.2 KCl, 1.15 g $Na_2HPO_4$, 0.2 g $KH_2PO_4$ in 1 liter deionized water, pH 7.2). The plate was then ready for assay, according to Part B.

Part B:

The protein binding sites were blocked by filling each well with blocking solution (5% bovine serum albumin) for 30 mins at room temperature. The plate was emptied and remaining droplets tapped out. Fifty microliters of monoclonal antibody (WI-MN-1) was added to each row except row #3, which was a control. The plate was incubated for 1–2 hours at room temperature. The plate was then emptied and tapped dry. The plate was then washed once by filling each well with 0.3 ml of wash solution (10 ml of wash solution concentrate supplied with the Hybri-Clonal™ Mouse G ELISA screening kit for monoclonal antibodies (purchased from Kirkegaard & Perry Laboratories, Inc. Gaithersburg, Md.))+190 ml deionized water. The plate was emptied and tapped dry. 0.05 milliliters of peroxidase labeled mouse gamma globulin antibody solution was added to each well. (0.05 milliliters horseradish peroxidase labeled antibody supplied with kit purchased from Kirkegaard & Perry Laboratories, Inc. described above)+0.50 milliliters diluent/blocking concentrate (10% bovine serum albumin)+4.50 milliliters of deionized water. Incubation was for 1 hr at room temperature. The plate was emptied and tapped dry. The plate was washed 5 times by filling wells with wash solution as above. The plate was then emptied and tapped dry. 0.05 milliliters ABTS substrate solution, which is 2,2'-azino-di[3-ethyl-benzthiazoline sulfonate] was added to each well (2.5 ml substrate solution A, 2.5 ml substrate solution B (supplied) from kit). Positive wells which turned blue-green were considered positive for presence of antigen bound by WI-MN-1 antibody. Plates were also automatically read for absorbance at 414 nm with the Titertek Multiskan (Flow Labs). An absorbance reading of two times over control was considered positive.

EXAMPLE III-3

Determining Molecular Weight of Isolated Antigen

The antigen on G-361 melanoma cell line was characterized by sodium dodecyl sulfate-polyacrylamide gel electrophoresis (SDS-PAGE).

Prior to SDS-PAGE, $1 \times 10^8$ G-361 melanoma cells were allowed to reach the log phase of growth. They were then washed with RPMI medium without leucine (GIBCO, Grand Island N.Y.) then suspended in 20 ml labeling medium (RPMI medium without leucine, to which $^3$H-leucine (2 mCi) (New England Nuclear, Boston Mass.) was added plus 10% fetal calf serum (GIBCO, Grand Island, N.Y.)), for 16 hours at 37° C. The cells were then harvested with and incubated in 10 mls Lysis reagent (10 mM Tris Buffered Saline (TBS) pH 7.5, containing 0.5% NP-40 (Nonidet P-40, purchased from Sigma, St. Louis, Mo.) and 1 mM phenylmethylsulfonyl fluoride) at 0° C. for 1 hour. The cells were centrifuged at 15,800×g for 30 minutes in an SS-34 model centrifuge (Sorvall, Newton N.Y.). The supernatant's CPM was determined by a beta counter. Non-specific binding was assessed by adding goat anti-mouse gamma globulin (Cappel, Cochranville, Pa. 19330) to the supernatant, for 15 minutes at 37° C., followed by 2 hours at 0° C. Protein A (The Enzyme Center, Inc., Malden Mass. 02148) was then added for 15 minutes at 37° C., followed by 0° C. for 1 hour. The mixture was then centrifuged at 2000 RPM (300×g) for 10 minutes. The supernatant was then removed and subjected to an immunoprecipitation procedure as follows: The WI-MN-1 antibody (100–300 µg, was added at 37° C. for 15 minutes, then put at 0° C. overnight. Goat anti-mouse gamma globulin IgG (Cappel, Cochranville, Pa. 19330) was then added and the mixture incubated at 37° C. for 15 minutes, then put at 0° C. overnight. The precipitate was centrifuged at 300×g to form a pellet. The pellet was washed twice with TBS+0.25% NP-40+0.1% SDS, then with TBS only. The resulting precipitate was dissolved in Laemmli sample buffer and subjected to the following procedure.

A stock gel solution was prepared consisting of 30% (w/w) acrylamide (Bio-Rad Laboratories, Richmond, Calif. 94804), and 0.8% (w/w) N,N'-bis-methylene acrylamide. Separating gel was prepared by mixing (all electrophorsis purity grade) 33.3 ml stock gel solution; 37.5 ml 1M Tris-HCl, pH 8.8; 1.0 ml 10% sodium dodecyl sulfate (SDS); 27.9 ml $H_2O$; 0.3 mls 10% ammonium persulfate (a fresh preparation of 0.1 g ammonium persulfate in 0.9 mls water); and 25 microliters N,N,N',N'-tetramethylethylene diamine (TEMED). Stacking gel was prepared by mixing: (all electrophoresis grade) 1 ml stock gel solution; 1.25 1M Tris-HCl, pH 6.8; 10% SDS; 7.595 ml $H_2O$; 30 microliters fresh 10% w/w ammonium persulfate; and 2.5 microliters TEMED. Electrophoresis buffer was as follows: 0.025M Tris-HCl, 0.192M glycine, 1% SDS. The gel was cast according to the method of Laemmli. King, J. and Laemmli, U. K., 62 *J. Mol. Biol.* 465–473 (1971). A molecular weight protein standard was purchased from Pharmacia and total protein amount of 2 µg was dissolved in sample buffer (1% SDS and 1% mercaptoethanol in 10 mM Tris-HCl, pH 8.0). Samples of purified antigen were measured for protein concentration, and a sample containing a total of 2 µg protein was dissolved in sample buffer. The dissolved standard and sample were then heated for 5 minutes at 100° C. Fifty µl of sample (2 µg protein) was applied to the 1.5 mm thickness gel. Running buffer was added to the lower chamber of the apparatus. Current (60 volts until the sample ran into the stacking gel, then 120 volts until the dye front migrated to within 1–2 cm of the bottom of gel) was applied for about 5 hours using a Biorad's Model 150A instrument. The molecular weight of the antigens was determined by removing the gel from the tubes, slicing each gel across the longitudinal axis into 2.5 mm pieces with a razor blade, and placing each piece in a scintillation vial (empty scintillation vial (5 ml volume)). 0.5 ml of 0.1% SDS and 0.25% NP-40 in 10 mM Tris-HCl was added to each vial overnight. Betaphase scintillation fluid (from West Chem Co., San Diego, Calif.) was added to each vial and the vials counted for $H^3$. A gel containing molecular weight standard proteins (14,400–94,000) was run simultaneously and stained with Coomassie Blue. The peak of $H^3$ activity in the gel slices was determined and the molecular weight thereof correlated with the standards. Two peaks of activity were obtained corresponding to about 105,000 M.W. and 38,000 M.W. with a maximum estimate of error of ±5000.

EXAMPLE III-4

Cell Sorter Analysis

Cell sorter analysis was done by preparing a suspension of cells of pleural effusion of a patient by centrifuging at 400×g for 10 minutes, washing twice with phosphate buffered saline (PBS), and suspending the cells in fresh PBS. The indirect immunofluorescence procedure was followed (as described in detail in Example III-1). An Epics V Cell Sorter Analyzer was used. The percentage of large, medium, and small cells having fluorescence, and therefore antigen capable of binding with WI-MN-1, was determined by analyzing diagrams generated by the instrument in response to the sample. Large cells were found to have 85% immunofluorescence, medium cells 21%, and small only 3%.

I claim:

1. A substantially pure soluble antigen capable of binding to monoclonal antibody produced by ATCC #HB8672, further characterized as being isolatable from G-361 melanoma cells and having a molecular weight as determined by sodium dodecyl sulfate gel electrophoresis of about 105,000 Da.

2. A substantially pure soluble antigen capable of binding to monoclonal antibody produced by ATCC #HB8672, further characterized as being isolatable from G-361 melanoma cells and having a molecular weight as determined by sodium dodecyl sulfate gel electrophoresis of about 38,000 Da.

* * * * *